(12) United States Patent
Ellingsen

(10) Patent No.: US 6,224,550 B1
(45) Date of Patent: May 1, 2001

(54) METHOD FOR MONITORING THE LEVEL OF AN OSMOTICALLY ACTIVE COMPONENT IN BODY FLUID AND DEVICE FOR CARRYING OUT SAID METHOD

(75) Inventor: Olav Ellingsen, Florø (NO)

(73) Assignee: Lifecare A.S., Florno (NO)

( * ) Notice: Subject to any disclaimer, the term of this patent is extended or adjusted under 35 U.S.C. 154(b) by 0 days.

(21) Appl. No.: 09/319,839

(22) PCT Filed: Dec. 22, 1997

(86) PCT No.: PCT/NO97/00349

§ 371 Date: Jun. 10, 1999

§ 102(e) Date: Jun. 10, 1999

(87) PCT Pub. No.: WO98/28605

PCT Pub. Date: Jul. 2, 1998

(30) Foreign Application Priority Data

Dec. 23, 1996 (NO) .................................................. 19965566

(51) Int. Cl.⁷ ....................................................... A61B 5/00
(52) U.S. Cl. ........................ 600/366; 600/345; 600/573; 600/584; 600/373; 204/403; 204/415
(58) Field of Search ..................................... 600/365–366, 600/373, 345, 347, 573, 584, 377; 73/64.47; 204/403, 406, 415–416

(56) References Cited

U.S. PATENT DOCUMENTS

| 3,187,562 | 6/1965 | Rolfson . | |
|---|---|---|---|
| 4,660,568 | 4/1987 | Cosman . | |
| 4,721,677 | * 1/1988 | Clark, Jr. | 600/365 X |
| 4,832,034 | * 8/1989 | Pizziconi et al. | 600/366 |
| 4,860,577 | 8/1989 | Patterson . | |
| 5,388,449 | 2/1995 | LeVeen . | |
| 5,695,623 | * 12/1997 | Michel et al. | 600/365 X |
| 5,711,861 | * 6/1965 | Ward et al. | 600/365 X |

* cited by examiner

Primary Examiner—Max Hindenburg
Assistant Examiner—Ryan Carter
(74) Attorney, Agent, or Firm—Welsh & Katz, Ltd.

(57) ABSTRACT

A method for monitoring changes in the level of an osmotically active component, such as for instance glucose, or in healthy humans, such as athletes for monitoring the level of lactic acid in the muscles is described. The key feature of the method is that the osmotic movement back and forth over a membrane is used to activate a sensing device, whereby the physical changes that take place in the fluid may be recorded by a receiver situated outside the body. A device for carrying out said method is likewise described.

4 Claims, 6 Drawing Sheets

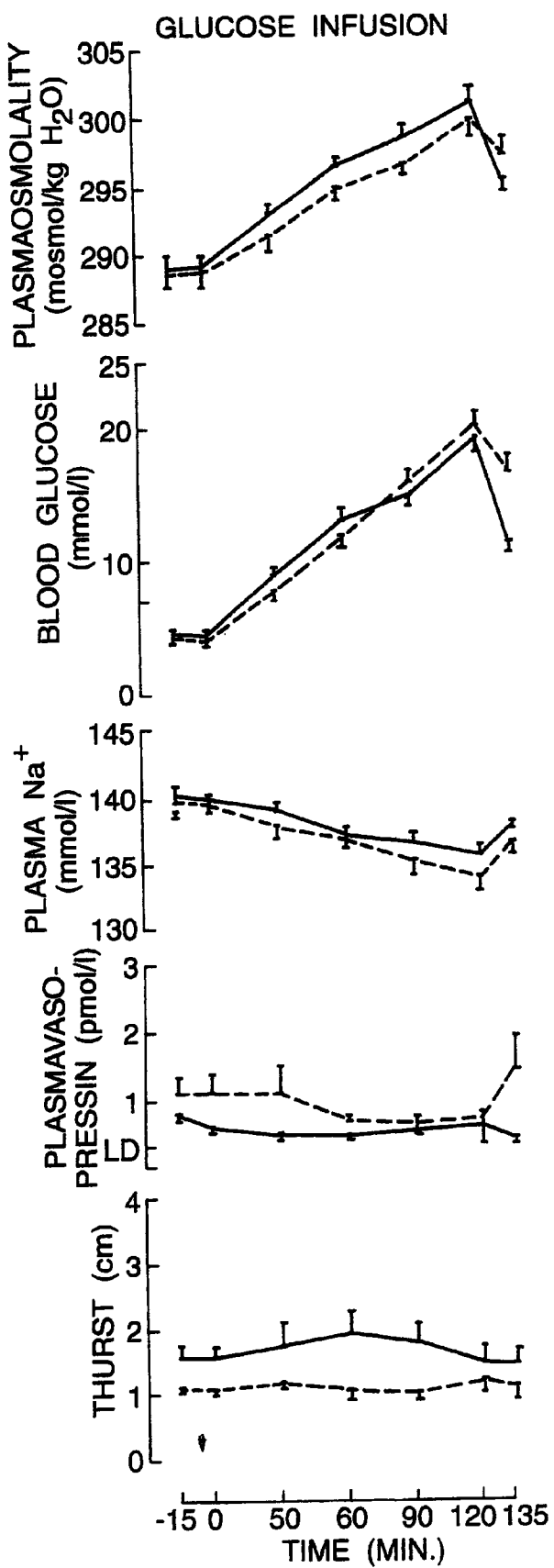

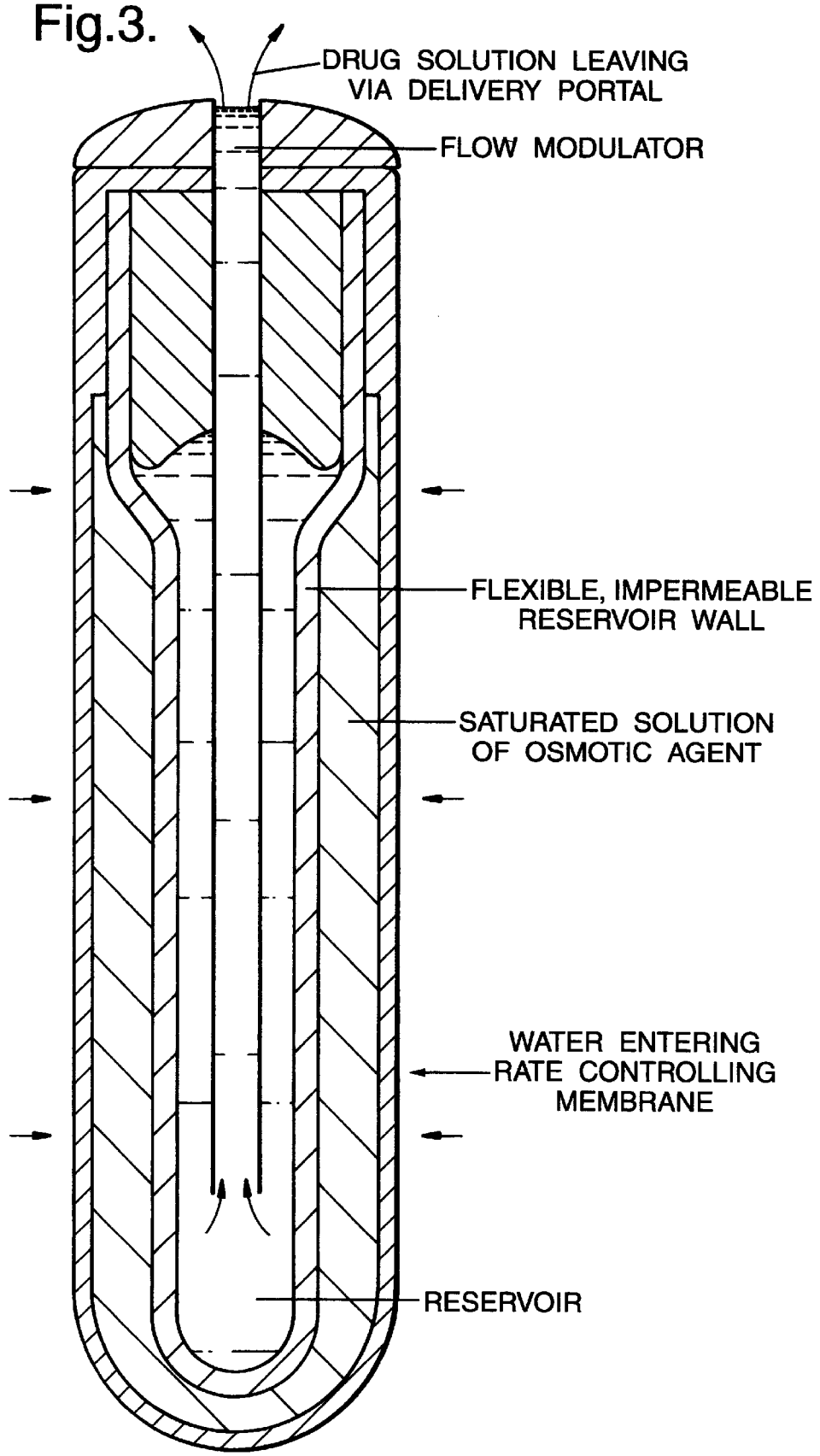

METHOD FOR MONITORING THE LEVEL OF AN OSMOTICALLY ACTIVE COMPONENT IN BODY FLUID AND DEVICE FOR CARRYING OUT SAID METHOD

FIELD OF THE INVENTION

The present invention is related to an implantable sensor for monitoring changes in the level of an osmotically active component, such as the glucose level in body liquid by detecting changed osmolality in the liquid across a semipermeable membrane.

BACKGROUND OF THE INVENTION

The present invention has utility with any osmotically active component in a body fluid, even though the following description, for simplicity, is focused on the monitoring of glucose.

It is a great demand, especially for persons suffering from diabetiesto monitor their glucose level in the blood as to gain a better regulation of the disease. Because of this, a number of different so called glucose metering system have been developed. One differs between two systems—invasive and non-invasive systems. Of these systems, it is the non-invasive system which has gained greatest interest and is currently used by thousands of people all over the world. The system is in principle based on a chemical reaction between a drop of blood and an oxidase on a so-called blood-stip. In its simplest form the glucose value can be evaluated by the changed colour on the strip, but more advanced systems includes an electronic recorder which calculate the actual value and shows it in display in mmol/l or mg/l. Even though the system is simple to operate, it has a number of drawbacks. It needs a sample of blood and this requires that persons have to pinch a hole in their finger to obtain this. And because of this, only a limited number of tests can be taken during a day, and the system can thus not monitor the glucose level continuously.

As regards invasive glucose sensors, a number of systems have been suggested and tried, but none of these have succeeded or been developed for practical use. The systems varies from implantable sensors based upon chemical reactions between blood and an oxidase, nuclear magnetic resonance, infrared light emission etc.

The objective of the present invention is to present an invasive sensor, especially a glucose sensor which can be implanted subcutaneously in interstitial liquid and where the level of glucose can be continuously monitored by an electronic detector outside the skin and where the electronic detector will show the values on a display, store the values and calculate average values over time, have an alarm for high and low preset values and at last, being able to calculate the need for insulin related to the actual level of glucose in the body and where this feature can be used to trigger an external or implanted insulin pump which altogether will act as an artificial pancreas.

The principle for the sensor is based upon osmosis.

In its simplest form, osmosis is the transportation of fluids across a semipermeable membrane separating two solvents with different concentration of solutes. The energy generated by the fluid flux activates the recording mechanism which can be an oscillating circuit or other means to detect the flux of water across the membrane in the current design.

The use of osmotic energy in a drug delivery system is known and in use. Felix Theeuwes describes in Journal of Pharmaceutical Sciences, 64: No.12, December 1975 the theory and principles related to the elementary osmotic pump, whereby drugs are delivered by an osmotic process at a controlled rate. Control resides in the: (a) water permeation characteristics of semipermeable membrane surrounding the formulated agent, and (b) osmotic properties of the formulation.

The use of osmosis as driving means for drug delivery systems is otherwise described by:

Sandra Z. Kernyi and Staynley L. Hartgraves, Oremature Excess Release From the Alzet Osmotic Pump, Pharmacology Biochemistry & Behavior, 27: pp. 199–201, 1987.

F. Theeuwes and S. I. Yum, Principles of the Design and Operation of Generic Osmotic Pumps for the Delivery of Semisolid or Liquid Drug Formulations, Annals of Biomedical Engineering, 4: 343–353, 1976.

Y. Sun, H. Xue, S. Janes, S. E. Sherman and D. L. Song, The use of an Alzet Osmotic Pump as a "Carryable" External Infusion Pump for Small Animal Studies, Proceed. Intern. Symp. Control. Rel. Bioact. Mater,. 17 (1990), Controlled Release Society, Inc., 17: 384–371, 1990.

As can be seen the osmotic principle and the use of this principle in drug delivery systems are well known.

SUMMARY OF THE INVENTION

The primary advantages of our design is the "multi stroke", self-calibrating, feedback loop which allow us to monitor the glucose level continuously. The published delivery systems based upon osmosis are all "one stroke" systems that inject a fluid at a steady state into the body with no feed-back device that can control the flow of drugs. Our design is "close-loop", since it continuously monitors the blood glucose levels and where the values are detected by the external detector.

Based upon the findings and the results from the different tests mentioned above the applicant wished to design an apparatus in the form of a housing with a semipermeable membrane and a calibrated fluid beneath the membrane being able to detect changes in the osmolality in the body fluid by osmosis and thus activating a sensing mechanism within the housing the semipermeable membrane may be a hollow fiber membrane, a sheet form membranme, or a corrugated membrane containing a osmotic calibrated fluid.

CONCISE DESCRIPTION OF THE DRAWINGS

FIGS. 2A–2K are graphs showing glucose infusion times vs. a variety of parameters;

FIG. 3 is a cross-section of an osmotic pump;

Figure 1:
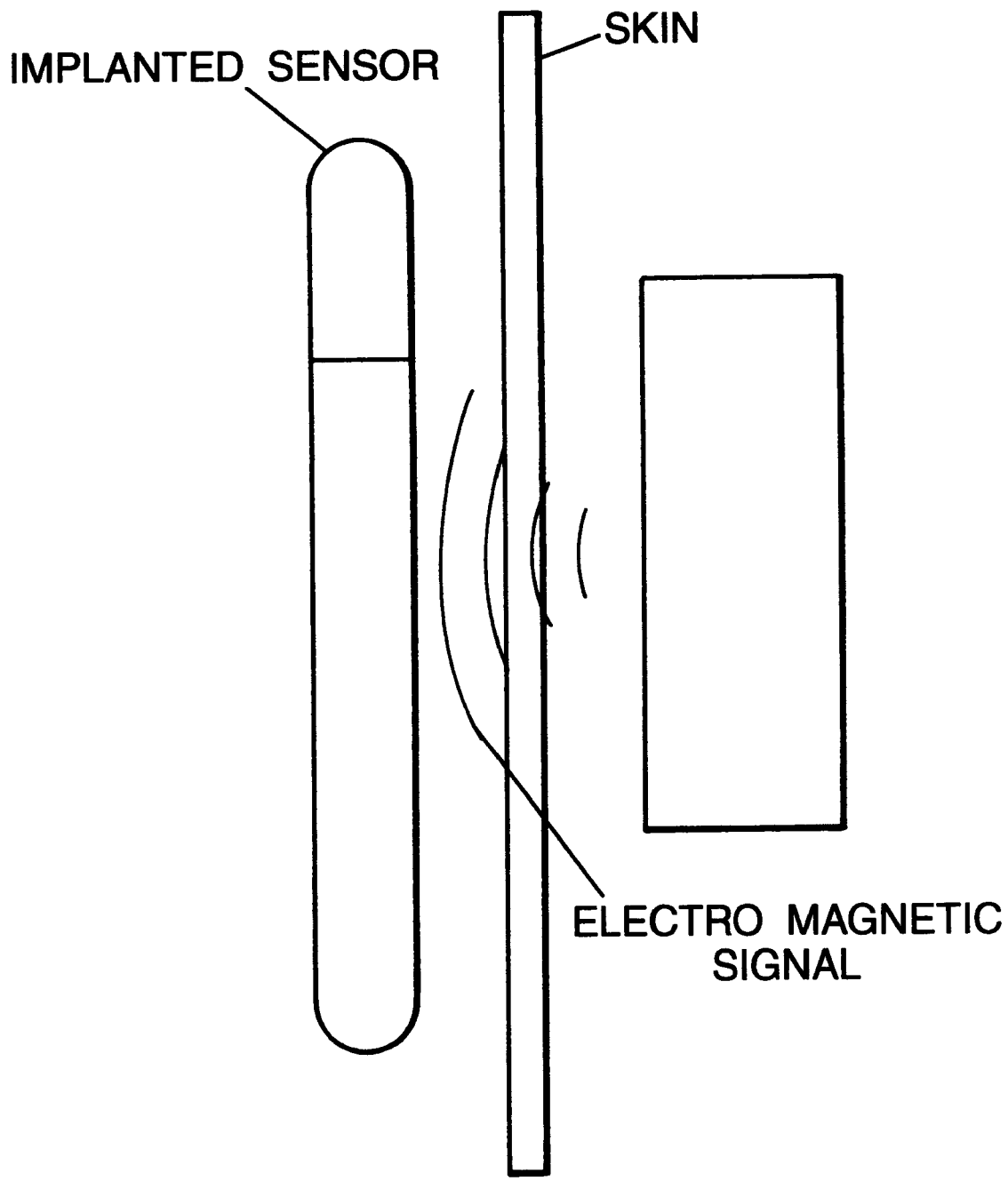
FIG. 1 is a schematic of the elements of the subject invention.
Figures 2F, 2G, 2H, 2I, 2J, 2K:
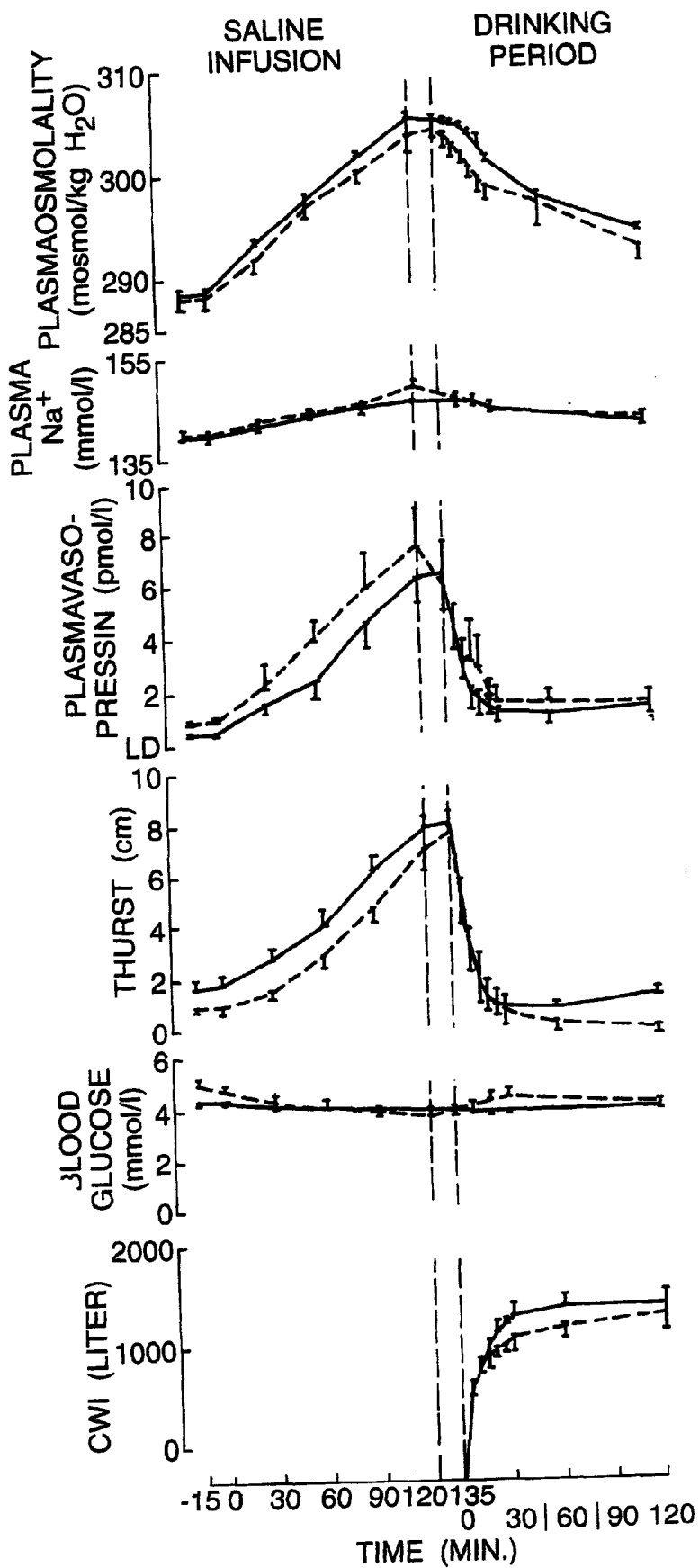

The principle and main functions of the invention is illustrated in FIG. 1.

The possible locations of the glucose sensor are primarily limited to areas of the body where blood glucose levels can be measured. The first obvious choice is blood itself. Unfortunately, blood is extremely combative to foreign bodies. Numerous in-vivo tests of glucose sensors in the blood have failed because the blood destroys the mechanism. Therefore the blood is an unacceptable site for a glucose sensor.

Interstitial liquid and peritoneal fluid contains glucose, more importantly, the static levels of interstitial and peritoneal fluid glucose parallel the blood glucose levels. Research on this field illustrates that body fluids are good indicators for the glucose levels of blood.

It is further reported in Encyclopedia of Medical Devices and Instrumentation, pg. 1413, 1989 that the extravascular sites has fluid which is primarily electrolyte, thus is nearly devoid of clotting elements (the most offensive of hostile substances), and usually has greatly reduces levels of most macromolecule.

Lastly, to locate the sensor outside the blood system provides an environment where the osmotic principle can be applied. Located under the skin or in the peritoneum, and effected by bodies natural encapsulation action, the changes in blood glucose levels will directly communicate to the device and initiate insulin delivery as required.

Osmosis; the tendency of a fluid to pass through a semipermeable membrane into a solution of higher concentration, so as to equalise concentrations on both sides of the membrane, is the basis of our glucose sensor. Simply illustrated, assume a semipermeable membrane separates a vessel into two equal volumes. The fluid on both sides of the membrane is a mixture of glucose and water. The membrane is impermeable to glucose.

For the experiments sake, increase the concentration of glucose on one side of this membrane. In an effort to equalise the concentrations of glucose on either side of the membrane, water will pass through the membrane into the side with higher glucose concentration. The transport of water across the membrane, will continue until eventually the concentration on glucose on both sides of the membrane becomes equal or the height of the water column in volume with the highest glucose concentration equals the osmotic pressure from the actual difference in glucose concentration between the two volumes.

In our system, the semipermeable membrane "senses" the difference of total osmolality between the calibrated fluid within the device an the body fluid outside the device. Osmolality is a function of the total number, or concentration, of molecules or ions present in the fluid, regardless the kind of molecules or ions. Osmolality is often expressed in mOsmol/l. For non-ionizing solutes, such as glucose, milliosmol of glucose per litter solvent equals the osmolality, but for solutes which disassociate into anions and cations, each ion is an osmotically active particle. For example NaCl will disassociate into $Na^+$ and $Cl^-$ ions such that each millimole of NaCl in solution will supply 2 milliosmol=mOsmol/l.

For example the osmolality of peritoneal liquid is approximately 280. This figure is the sum of the number of molecules and ions, of the different components in the peritoneal liquid, ie. Na (Sodium), K (Potassium), Cl (Chlorine), $CO_2$ (Carbon Dioxide), Ca (Calcium), Phosphorous, Urea, and Creatinine. (Konecke et al., 1980)

TABLE 1

Electrolyte concentration in peritoneal fluid and plasma

|  | Plasma | Peritoneal fluid | P value |
|---|---|---|---|
| Sodium (mol/liter) | 139,0 ± 3.2 (28) | 136,0 ± 0.7 (36) | 0.017 |
| Potassium (mmol/liter) | 5,2 ± 0.7 (28) | 3,9 ± 0.1 (36) | 0.051 |

TABLE 1-continued

Electrolyte concentration in peritoneal fluid and plasma

|  | Plasma | Peritoneal fluid | P value |
|---|---|---|---|
| Chloride (mmol/liter) | 102,8 ± 1.4 (67) | 110,6 ± 4.2 (86) | 0.001 |
| Carbon Dioxide (mmol/liter) | 16,3 ± 0,3 (67) | 22,4 ± 2.1 (86) | 0.012 |
| Calcium (mg/dl) | 8,3 ± 0.2 (28) | 7,4 ± 0.1 (86) | 0.001 |
| Phosphorous (mg/dl) | 2,9 ± 0.1 (67) | 2,6 ± 0.1 (86) | 0.003 |
| Urea (mg/dl) | 20,4 ± 0.7 (67) | 21,1 ± 0.6 (86) | NS |
| Creatinine (mg/dl) | 0,8 ± 0.2 (67) | 0,7 ± 0.01 (86) | 0.001 |

The mean ± SE and the number of determination (in parentheses are indicated) Osmolality 280 mOsmol/I.

Therefore, if the calibrated fluid has an osmolality of 280 mOsmol/l, exactly in the proportions of the chart above, and the glucose in the body fluid rises, the osmolality of the body fluid will therefore be greater than 280 mOsmol/l. Since the membrane is impermeable to glucose, a water flux from within the device will occur. The water flux will attempt to equalise the osmolality on either side of the membrane by lowering the concentration of the glucose, and thereby lowering the osmolality.

Energy is generated by the flux of water across the membrane. The duration and magnitude of the energy is directly proportional to the amount of glucose poured into one side of the vessel. Specifically, a larger quantity of glucose will cause a stronger flux for a longer period of time. This is the energy we will use to control insulin delivery.

Griffith states, in Introduction to Human Physiology, page 52, that "The magnitude of the osmotic pressure of a solution depends upon the number of particles of solutes present in a unit volume of water rather than upon the chemical nature of the solute."

Successful operation of the osmotic glucose sensor is contingent upon the fluctuation body fluid osmolality, and, in our situation directly proportional to the present glucose gradient. As expected, glucose does effect the osmolality of the body. As illustrated in the graphs below (C. J. Thompson et al.: Clin. Science 74: 599–606, 1988) the increase of body osmolality, due to glucose gradient, is sufficient to operate the device.

Furthermore, as mentioned above, the glucose levels in the interstitial liquid or peritoneal fluid are directly proportional to blood glucose levels. Therefore, the osmolality gradient in these fluids should also parallel the osmolality gradient in blood plasma. The fluid located inside of our device will include fluid with an osmolality equal to that of normal concentration of glucose. The fluid inside the device will be separated from the body fluids by a membrane similar to the membrane in the example above. As the glucose rise in the body fluids, outside of the device, fluid from within the device will exit the device in an effort to equalise the concentration of glucose on both sides of the membrane. The energy associated with the fluid leaving the device will be used to activate the sensing mechanism in the sensor.

As the glucose levels decreases in the body fluids a little under its normal level, due to the release of insulin, the osmolality in the body fluids will become less than the osmolality in the device. The osmotic principle will take over again, but now in the opposite direction. Fluid will return to the device, and activate the sensing mechanism in the opposite direction.

The fluids on both sides of the membrane will then have equal osmolality and, therefore, are prepared to respond to the next increase in glucose, which increases the osmolality.

Osmotic pumps have been used extensively in-vivo for a number of years. Specifically, Alza Corporation, of Palo Alta, Calif., U.S.A. has used single stroke osmotic pumps for continuous drug delivery research in animals—FIG. 3. Alza research has produced a number of interesting results.

The Alza pumps described above are single stroke devices and our design are a multy stroke design. In other words, the Alza pump delivers drug at a continuous rate until the drug reservoir empties. The osmotic energy is used to squeeze the drug from a collapsible reservoir. Our design uses the same osmotic energy as Alza's pump, except we use the energy to initiate an sensing mechanism, rather than squeeze a reservoir.

The information referenced above can be used to predict the feasibility of our multistroke device. The statements can be interpreted, when in the context, as a meaning that the osmotic principle is well understood and the energy associated with the osmotic action can be accurately predicted by appropriate formulas. Additionally, the predicted values has been verified by in-vitro tests results.

Furthermore, the actual osmotic energy realised during in-vivo tests is substantially equal to the predicted values and also equal to the in-vitro values.

One of the major concerns of any glucose sensor is the calibration of the device. Incorrect calibration can result in faulty measurement of glucose level and eventually inappropriate administration of insulin. The glucose sensor must continually adjust itself to the level of glucose which is "normal" for the current physiological condition of the patient.

For example; if the device is designed to also administer insulin and is permanently calibrated to the "normal" level of body fluid osmolality, including glucose, at the level "X", any rise of osmolality above "X" should initiate delivery of insulin. This is acceptable if the "normal" osmolality in the body is constant at "X". If the "normal" osmolality in the body drops below "X", to "X-N", the device will not administer insulin until the osmolality level, rises above "X". Therefore the body realise a rise of glucose equal to "N" before any insulin is administered to counteract on this rise. This is especially harmful if "N" is a significant amount.

The same scenario could occur if the "normal" osmolality of the body rises above "X". In this scenario, the device would incorrectly administer insulin until the osmolality dropped back to "X", This scenario is obvious dangerous. These situations will not occur with the device according to the present invention.

Our glucose sensor accomplishes self-calibration through the characteristics of the membrane. In our osmotic design, the osmolality in the fluid within the device, controls the level of glucose in the body. In the body fluid there are only two solutes that can increase by a magnitude of several hundred percent within minutes, namely glucose and lactic acid. These solutes will raise the osmolality of the body fluid and cause the device to administer insulin when hooked up ton an insulin pump.

To avoid activation of the device by increased Lactic Acid we have considered a number of physiological and design issues. Physiologically, the Lactic Acid in the body fluids appear to be less than in blood plasma and therefore does not have the same "triggering effect" as might be expected. To avoid any interference by changed osmolality due to any acids, we do not suggest the system to be used for insulin administration when rise in lactic acids might occur, as during hard exercises.

Certain illnesses, and other circumstances, may cause the total osmolality in the body fluid might change over time (hours and days). If the osmolality in the calibrated fluid where kept constant, we might realise a scenario as mentioned above. The calibrated fluid in the device must parallel this "normal" body osmolality to remain properly calibrated. The slow fluctuation in total osmolality is the result of changes in the concentration of solutes within the body fluids. Since the membrane do not respond to other than glucose and Lactic Acid, the concentration of solutes in the body and calibrated fluid will remain equal. Simply stated, the solutes will flow freely through the membrane and equalise the concentration on both sides of the membrane.

The total osmolality in the body is also dependent on the concentration of glucose and lactic acid. Although the membranes respond to rapid fluctuations in glucose and lactic acid, it does not respond to slow gradients of these two solutes. During our tests, the membranes have shown ability to pass at least 1.5 mmol/l of glucose or lactic acid every 24 hours. Therefore, if the "normal" or basal total fluid osmolality fluctuates due to slow changes in glucose or lactic acid, as well as any other solute, the device will remain calibrated. This transport of small solutes into the device, by diffusion, the Donnan effect, solvent drag and filtration, will adjust the calibrated liquid to parallel the fluctuating "normal" osmolality in the body fluid. This automatic, self-calibration is a function of the membrane characteristics, and is required for all glucose sensors.

This self calibration is assisted by the body osmolality self calibration. If the body fluid osmolality rises above normal levels, the cells absorb Na (Sodium) to counteract the increase of osmolality and avoid dehydration. This decrease of sodium in the body fluid osmolality, and "assist" with the self-calibration of our device.

Finally, to avoid dehydration of the cells, the body will reduce the sodium in the body fluid to compensate for the increase in the osmolality. This takes place within approximately 60 minutes after the increase of glucose or lactic acids. The device must respond before the osmolality drops because of sodium compensation. This response time is built into the design of our device.

The semi-permeable membrane is the heart of the glucose sensor as it's function is to "feel" the level of glucose in the body fluid. The characteristics of the membrane, compared to the calibrated fluid within the device and the body fluid outside ar the key relationships of the glucose sensor. The function of the membrane is to "sense" the osmolality outside of the device, with respect to the osmolality of calibrated fluid, and facilitate the largest osmotic flux possible.

Ideally, the membrane will be highly sensitive to glucose gradients and no response to gradients of any kind of other solutes in the body fluid. Control resides in the water permeation characteristics of semipermeable membrane surrounding the formuletion agent linearity of response from 1 to 15 mmol/l of glucose.

The membrane should be biocompatible.

It should be stable and consistently sensitive when exposed to various environments.

The membrane should facilitate response of device to glucose gradient in less than 10 minutes.

Sorensens et al. Physiologic Pharmacokinetics model of glucose homeostasis; DiabetesCare, 5:, No.3, 148–157, May–Jun 1982 using a theoretical pharmacokinetics model of glucose homeostasis showed that the increases in sensor delay resulted in progressive loss in glucose regulation, exacerbation of hyperinsulinemia, and increased insulin requirements. Further Sorensens model predicted that increasing the glucose measurement time delay from 1.5 to 30 min. would result in nearly tripling insulin requirement.

Membrane technology an the theory of solutes through semipermeable membranes by diffusion, the Donnan effect, filtration and osmosis is well understood and documented. In fact, these phenomena are basis for all fluid and solute transport in the body in addition to the ionic pump activated by ATP.

Extensive research has been completed to find membranes with the appropriate characteristics. The optimal combination of membranes and calibrated fluid (formulation agent) has been one of the primary goals for our research.

As a results of this research we have selected a number of membranes with appropriate flux, stability and sensitivity characteristics.

We have found a linear flux rate proportional to glucose gradient across the membranes. More correctly stated, we found a linear flux rate in proportion to the osmolality change due to a glucose gradient.

In addition to glucose, the membranes have been tested with all other solutes which change the osmolality in the peritoneum, such as urea, lactic acid, NaOH-butyrate, NaCl and phosphorous.

When exposed to physiological urea gradients, the membrane did not cause any osmotic effect. Furthermore, with lactic acid and salts in peritoneal like fluid (PLV), we did not record twice the flux for each mmol of these substances because of it's disassociation of anions and cations, as theoretically expected.

W. F. Ganong states in Review of Dedical Physiology; 9th ed., p. 10, that the freezing point of normal human plasma averages $-0.54°$ C., which corresponds to an osmolal concentration in plasma of 290 mOsm/l. This is equivalent to an osmotic pressure of 7.3 atmospheres. The osmolality might be expressed to be higher than this, because the sum of all the cation and anion equivalents in plasma is over 300. It is not this high because plasma is not an ideal solution, and ionic interaction reduces the number of particles free to exert an osmotic effect. Except when there has been insufficient time after a sudden change in composition for equilibrium to occur, all fluid compartments in the body are apparently in or nearly in osmotic equilibrium. The term toxicity is used to describe the effective osmotic pressure of a solution relative to plasma. Solutions that have the same effective osmotic pressure as plasma are said to be isotonic, those with greater pressure is said to be hypertonic, and those with lesser pressure are hypotonic. All solutions that are isosmotic with plasma—ie. have the same actual osmotic pressure or freezing point depression as plasma—would also be isotonic if it were not for the fact that some solutes diffuse into cells and other are metabolised. Thus, a 0.9% saline solution is isotonic because there is no net movement of the osmotically active in the solution into the cells and the particles are not metabolised. However, urea diffluses rapidly into cells, so that the effective osmotic pressure drops when cells are suspended in an aqueous solution that initially contains 290 mOsm/l of urea! Similarly, a 5% glucose solution is isotonic when initially infused intravenously, but glucose is metabolised, so net effect is that of infusing hypotonic solution.

What is explained here, and has been illustrated by our research, is that urea does not have any osmotic effect—event if it should change rapidly. Furthermore, we have found that the osmotic effect of lactic acid should is less than theoretical expected. In the case that lactic acid produces a "false trigger", we have developed a number of proprietary means to counteract the effect.

Stability and sensitivity was illustrated by testing the membranes in various solutions. The results showed that the membranes retained their specific flux in one solution after exposure in a number of other solutions. In other words, there is no membrane destruction due to exposure to various solutions investigated. The membranes were the tested under non-sterile conditions which resulted in excessive growth of bacteria on the membrane surface. The bacteria growth did not affect the flux characteristics of the membrane in short term experiments (weeks).

The membranes have shown promising biocompatibility. Nevertheless, we have identified a number of vehicles to improve the biocompatibility, and reduce or eliminate the long term effects of implantation. Our methods to improve biocompatibility and extend the life of the device includes the selection of implant location, material selections (such as coat of hydrogel, various titanium protective designs). A combination of a "safer" environment, proper design and materials selection will provide a biocompatible environment for the device.

With the device implanted subcutant or in the peritoneum, our biocompatibility issues will be greatly reduced and are manageable. As an additional measure we have employed a number of materials in the design of our device which may greatly reduce or eliminate fibrous growth and deterioration of the device.

The response time of the system is the period between the start of the glucose gradient and the start of the sensing mechanism. The response time depends on the following factors:

1. The specific membrane flux characteristics expressed in $q_c$=approx. 0,80 [$mm^3/cm^2 mmol h$]—Osmotic Flux Data obtained on RO membranes by varying gradients of glucose.
2. The effective membrane surface area A $cm^2$. With the hollow fibre membranes glucose sensor as in FIG. 1 with, the effective membrane area is approximately 75 [$cm^2$].
3. The volume (V) of calibrated fluid, evacuated from the device, needed to activte the sencing mechanism.
4. The rate of glucose gradient=C.

Figure 4:
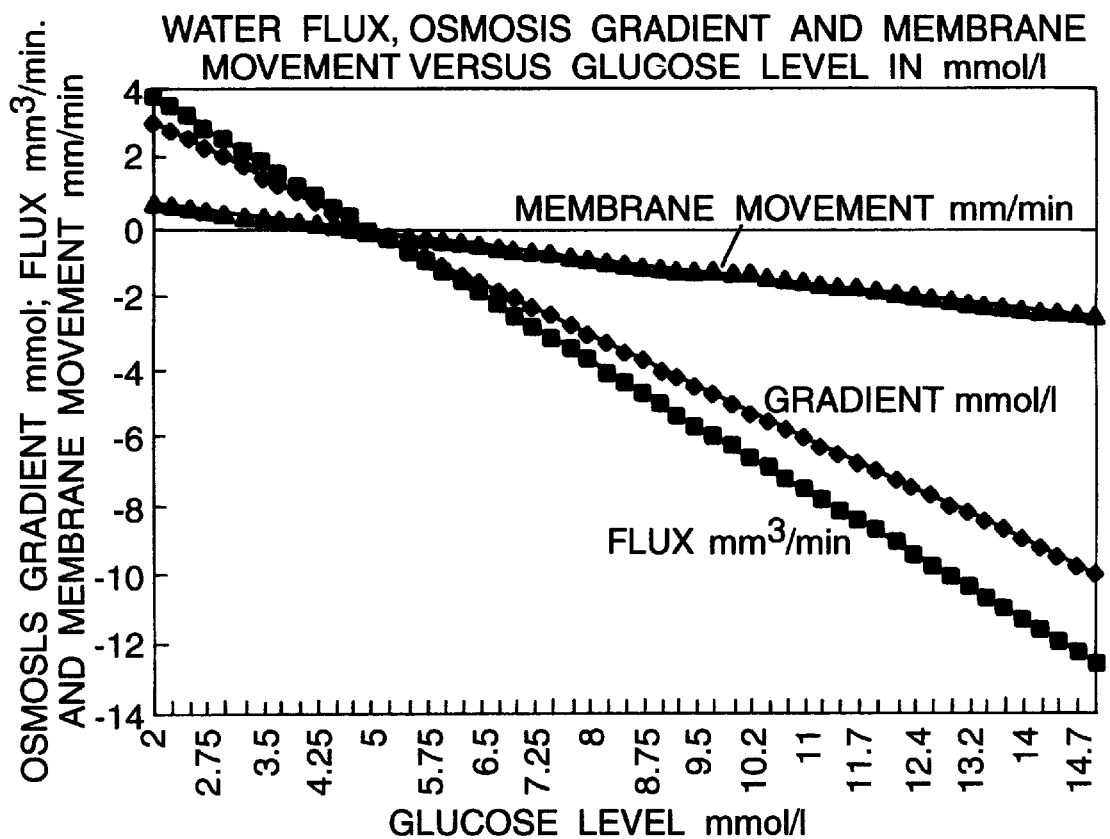
FIG. 4 is a graph of water flux, osmosis gradient and membrane movement vs. Glucose level.
Figure 6:
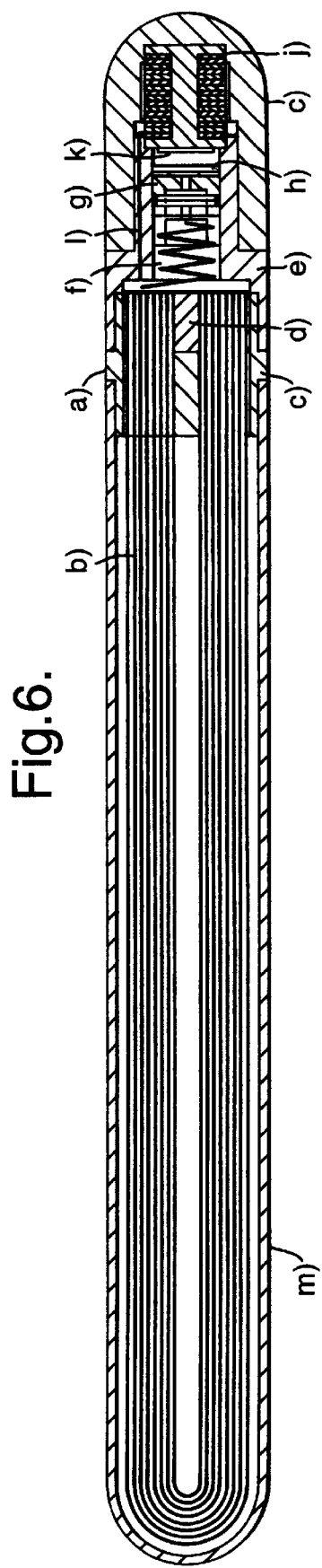
FIG. 6 is a cross section of a preferred embodiment of the subject invention.

Based upon the shown design in FIG. 6 of the enclosed drawings, we have performed calculations of the water flux, osmoses gradient and movement of the <<floating>> membrane on the sensing device as shown in FIG. 4.

Figure 5:
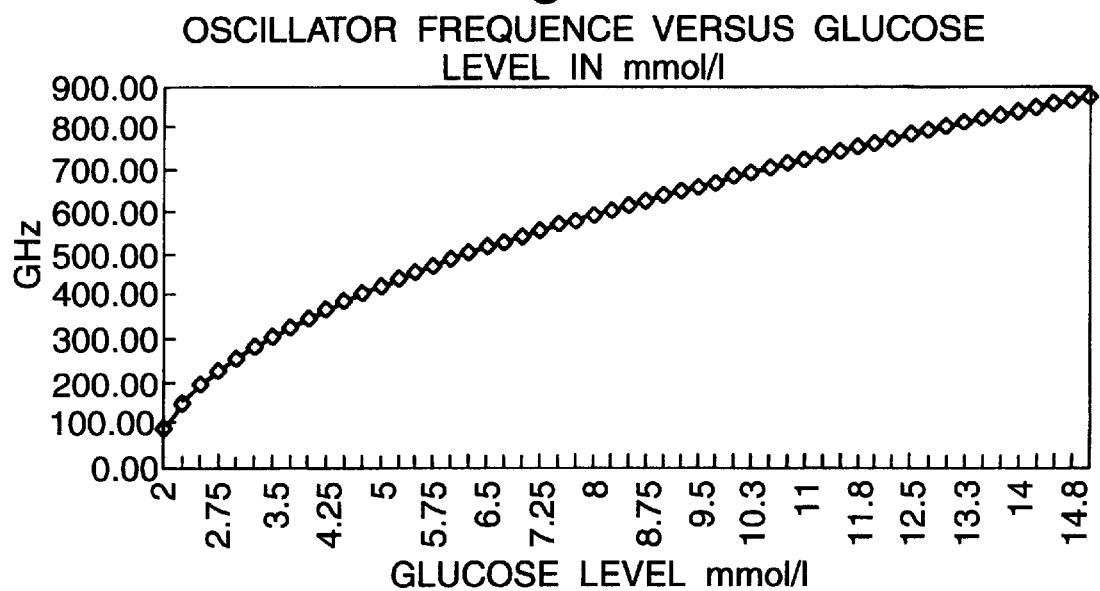
FIG. 5 is a graph of oscillator frequency vs. glucose level.

When the sensing device is an oscillating circuit where the frequency of the circuit is changed by changing the capacitance of an capacitor where the flux will change the gap between the capacitor plates as shown in FIG. 6 in the enclosed drawings, the frequency is changed in accordance to FIG. 5.

This show clearly that we have a distinct variation of the oscillators frequency by small variations of the glucose level in the body.

In the device according to the invention the function of the housing is in containing the glucose sensor components, ie. the membrane, sensing device and the calibrated fluid. Other than a host for the glucose sensor, the housing has an indirect function. The housing must be as "human friendly" as possible through its weight and biocompatibility. Thus the housing has to be produced by a highly biocompatible material.

As host for the glucose sensor, the housing is located either directly under the skin or in the peritoneum, as explained above for the sensor.

Based upon the different membrane characteristics, the sencing arrangement, and implantation procedures and locations, the housing can take a number of different shapes. One embodiment is a disc shaped housing with (2)

membranes, one on each side. The calibrated liquid beneath the membranes will communicate so that the total effective membrane area is the sum of both membrane surfaces.

Another embodiment where the housing is cylindrical, the membrane is corrugated which allows for greater membrane surface area.

An still another embodiment as shown in FIG. 1 can be a cylindrical housing where hollow fibre membranes are casted into the one end of the housing and the membranes being protected with a biocompatible sill, such as laser perforated titanium. This will protect the membrane from macromolecule and proteins formations We have looked for a biocompatible material with a density as close to water as possible. This specific density will avoid any difference in the acceleration between body tissue and the implant. Therefore, the material must be a plastic or titanium.

Medical grade polyurethane is an alternative as wells as derivates from polyanhydrides or polyacetate, which are a classes of biocompatible polymers that appear practically suitable for drug delivery systems.

The aim of the biocompatibility is facilitate the growth of soft tissue around the implant to ensure proper saturation of the semipermeable membrane.

The monitoring device is an electronic circuit which scans the frequency of the sensor similar to a radio. When the monitoring device frequency matches the frequency of the sensor, a <<dipp>> of the signals will appear and which will be identical with the actual glucose level.

The preferred embodiment is explained further in detail with reference to FIG. 6 of the enclosed drawing:

a) shows a cylindrical part of the device where a bundle of hollow fibre membranes b) are casted into a). The fibres are put into four or more holes c) and is casted into epoxy at d). Upon a) a housing e) is attached which have a cylinder bore f) wherein is located a floating piston g) in non conductive material. On the piston is attached a metal plate h) acting as the one plate in the capacitor. Upon the housing e) is attached another housing i) where a magnetic coil j) is located. On the end of the coil is attached a metal plate k) acting as the other plate of the capacitor. The capacitor and the coil is connected with the wires l).

Inside the hollow fibre membranes and the cylinder f) is located a fluid with a <<normal>> body osmolality as described above. When water is entering the hollow fibre due to decreased glucose level in the body, the floating piston moves upwards and reduces the gap between the capacitor plates. When water leaves the hollow fibre membranes and the cylinder as is the case when the glucose level rises, the floating piston moves downwards and the gap between the capacitors increases.

Over the bundle of the hollow fibre membranes is located a sill m) attached to a).

It is obvious that the physical displacement of the liquid can be arranged to activate a number of different sensing devices which can be recorded by a signal outside the body. Such devices may be a pressure sensor, microphone etc.

The monitoring device is in its simplest form an variable oscillating circuit which can scan the spectra of the variable frequencies of the sensor. The values are presented in a display calibrated as mmol/l or mg/l of glucose. The device can be equipped with storing capacity of data and a small computer program to calculate average glucose levels and a mathematical program to calculate the insulin requirements relative to the level of glucose. Further more the device can be equipped with alarm for high and low glucose values.

What is claimed is:

1. Method of monitoring the changes in the level of an osmotically active component in a body or for monitoring the level of lactic acid in muscles, wherein an osmotic movement in a fluid back and forth over a membrane is used to activate a sensing device, whereby the physical changes that take place in the fluid may be recorded by a receiver situated outside the body.

2. Method according to claim 1, wherein the membrane used is a hollow fiber membrane, a sheet formed membrane or a corrugated membrane containing an osmotic, calibrated fluid, which fluid is placed in contact with a void in the device where means for monitoring/detecting volume changes of he calibrated fluid as a result of the flux of fluid through the membrane are present.

3. Method according to claim 2 wherein the monitoring/detection of the volume change is effected by action on an oscillating circuit arranged in a housing of the device, whereby the frequency of the oscillating circuit is changed in relation to the volume changes, in a manner selected from the group consisting of changing the gap between the capacitors and changes of the inductance of a coil, in that the volume changes may affect any detector means that is able to generate a signal that may be recorded in a certain distance from the device.

4. Device for carrying out the method according to claim 1 wherein said device comprises a receiver consisting of variable oscillating circuit that is able to record the oscillating circuit in a sensor and wherein the corresponding frequency is presented in a display in a value relevant to the measurement in question, as a suitable unit, and means for storing the recorded a data, whereby the device also comprises a means for calculating average values, and also comprising an integrated circuit which with the help of an algorithm is capable of computing the need for medication related to the measured values, and whereby the device optionally is equipped with an alarm for preset height and low values.

* * * * *